United States Patent
Lee et al.

(10) Patent No.: US 9,536,298 B2
(45) Date of Patent: Jan. 3, 2017

(54) ELECTRONIC DEVICE AND METHOD FOR DETECTING SURFACE FLAW OF OBJECT

(71) Applicant: Shenzhen Airdrawing Technology Service CO., LTD., Shenzhen (TW)

(72) Inventors: Hou-Hsien Lee, New Taipei (TW); Chang-Jung Lee, New Taipei (TW); Chih-Ping Lo, New Taipei (TW)

(73) Assignee: Shenzhen Airdrawing Technology Service Co., Ltd, Shenzhen (CN)

( * ) Notice: Subject to any disclaimer, the term of this patent is extended or adjusted under 35 U.S.C. 154(b) by 305 days.

(21) Appl. No.: 14/334,907

(22) Filed: Jul. 18, 2014

(65) Prior Publication Data

US 2015/0022657 A1    Jan. 22, 2015

(30) Foreign Application Priority Data

Jul. 19, 2013  (TW) .............................. 102125840 A (51) Int. Cl.
*H04N 7/18*    (2006.01)
*G06T 7/00*    (2006.01)

(52) U.S. Cl.
CPC .................................... *G06T 7/001* (2013.01)

(58) Field of Classification Search
CPC ..................................................... G06T 7/001
USPC ......................................................... 348/129
See application file for complete search history.

(56) References Cited

U.S. PATENT DOCUMENTS

| | | | | |
|---|---|---|---|---|
| 2006/0182334 A1* | 8/2006 | Akimoto | .......... | G01N 21/95607 382/145 |
| 2012/0147919 A1* | 6/2012 | Hisanaga | ............... | G01B 11/25 372/50.23 |
| 2012/0263347 A1* | 10/2012 | Ichimaru | ............ | G01B 11/2518 382/103 |

* cited by examiner

*Primary Examiner* — Allen Wong
(74) *Attorney, Agent, or Firm* — Zhigang Ma (57) ABSTRACT

Method for detecting a surface flaw of an object using an electronic device includes requesting a detection device to control a camera unit to capture a current image of a test object placed on the detection device. The current image includes a sidewall image and a reflected image. The method obtains the current image, and detects whether the sidewall image has a surface flaw. When the sidewall image has a surface flaw, a rotation angle of the test object is determined based on the reflected image. The method obtains a standard sidewall image of a standard object stored in a storage device of the electronic device, based on the rotation angle, compares the sidewall image with the standard sidewall image, and determines and displays a position of the surface flaw on a sidewall of the test object based on the comparison.

18 Claims, 11 Drawing Sheets

ELECTRONIC DEVICE AND METHOD FOR DETECTING SURFACE FLAW OF OBJECT

CROSS-REFERENCE TO RELATED APPLICATIONS

This application claims priority to Taiwanese Patent Application No. 102125840 filed on Jul. 19, 2013 in the Taiwan Intellectual Property Office, the contents of which are incorporated by reference herein.

FIELD

Embodiments of the present disclosure relate to inspection technology.

BACKGROUND

An object (e.g. a phone) being tested can include surface flaws. Surface flaws can be detected on an object, but a specific position of the surface flaw of the object usually cannot be detected.

BRIEF DESCRIPTION OF THE DRAWINGS

Many aspects of the disclosure can be better understood with reference to the following drawings. The components in the drawings are not necessarily drawn to scale, the emphasis instead being placed upon clearly illustrating the principles of the disclosure. Moreover, in the drawings, like reference numerals designate corresponding parts throughout the several views.

DETAILED DESCRIPTION

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. Also, the description is not to be considered as limiting the scope of the embodiments described herein. The drawings are not necessarily to scale and the proportions of certain parts have been exaggerated to better illustrate details and features of the present disclosure.

The present disclosure is illustrated by way of examples and not by way of limitation. It should be noted that references to "an" or "one" embodiment in this disclosure are not necessarily to the same embodiment, and such references mean "at least one."

Furthermore, the term "module", as used herein, refers to logic embodied in hardware or firmware, or to a collection of software instructions, written in a programming language, such as, Java, C, or assembly. One or more software instructions in the modules can be embedded in firmware, such as in an EPROM. The modules described herein can be implemented as either software and/or hardware modules and can be stored in any type of non-transitory computer-readable medium or other storage device. Some non-limiting examples of non-transitory computer-readable media include CDs, DVDs, BLU-RAY, flash memory, and hard disk drives.

Figure 1:
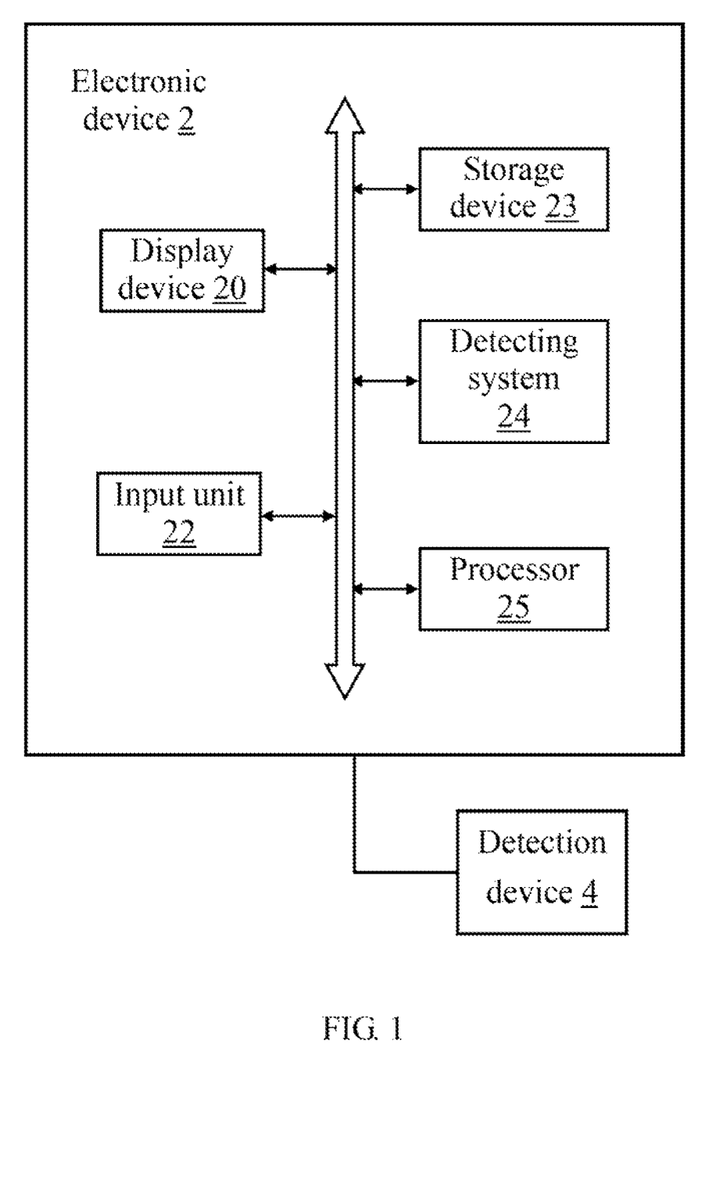
FIG. 1 is a block diagram of one embodiment of an electronic device including a detecting system.

FIG. 1 illustrates a block diagram of one embodiment of an electronic device 2. Depending on the embodiment, the electronic device 2 includes a detecting system 24. In one embodiment, the electronic device 2 can be a tablet computer, a notebook computer, a mobile phone, or any other electronic device. The electronic device 2 includes, but is not limited to, a display device 20, an input unit 22, a storage device 23, and at least one processor 25. The display device 20 displays data of the electronic device 2. The input unit 22 can be a mouse or a keyboard.

In at least one embodiment, the storage device 23 can include various types of non-transitory computer-readable storage media. For example, the storage device 23 can be an internal storage system, such as a flash memory, a random access memory (RAM) for temporary storage of information, and/or a read-only memory (ROM) for permanent storage of information. The storage device 23 can also be an external storage system, such as a hard disk, a storage card, or a data storage medium. The at least one processor 25 can be a central processing unit (CPU), a microprocessor, or other data processor chip that performs functions of the electronic device 2.

Figure 4:
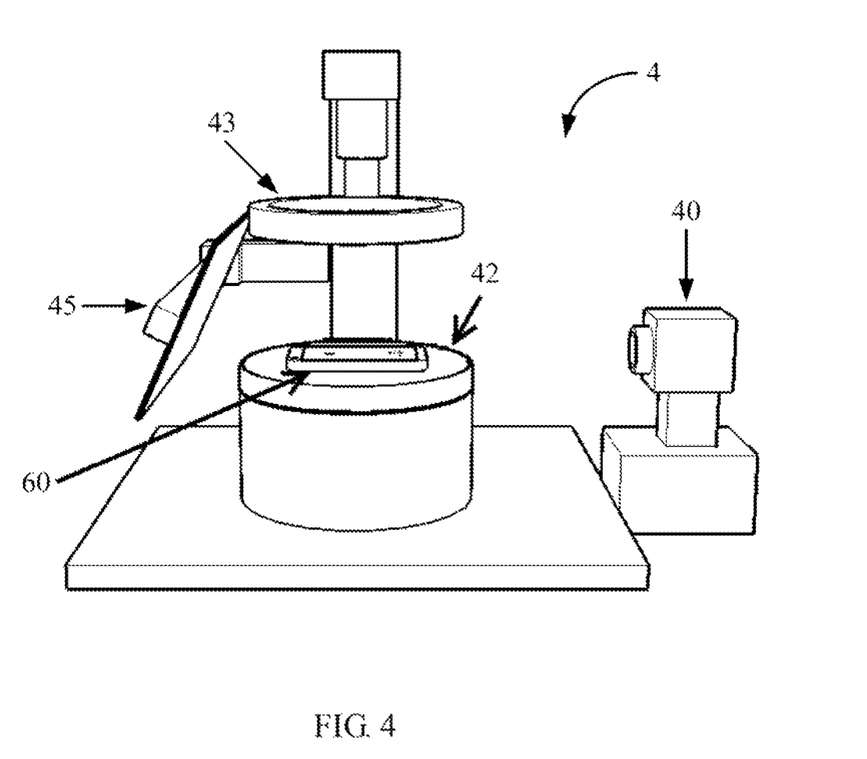
FIG. 4 is a perspective view of one embodiment of a detection device in communication with the electronic device in FIG. 1.

In one embodiment, the electronic device 2 is connected to a detection device 4 through a data cable (not shown). As shown in FIG. 4, the detection device 4 includes, but is not limited to, a camera unit 40, a horizontal rotating platform 42, a light source 43, and a plane mirror 45.

As shown in FIG. 4, an object to be tested (hereinafter "test object 60") is placed on the horizontal rotation platform 42. The test object 60 is fixed on the horizontal rotation platform 42 through a fixing unit (not shown). The fixing unit can prevent the test object 60 from moving when the horizontal rotation platform 42 rotates to different angles. The light source 43 is positioned directly above the test object 60. The horizontal rotation platform 42 includes a first side and a second side opposite to the first side. The camera unit 40 is arranged on one of the first side and the second side, for example, on a right hand side. The plane mirror 45 is connected to the other side of the first side and the second side, for example, on a left hand side, and is oriented at a certain angle, such as eighty degrees. Thus the plane mirror 45 forms an image of the test object 60 placed on the horizontal rotation platform 42. As an example shown in FIG. 5, the image formed by the plane mirror 45 includes a top surface and two sidewalls of the test object 60. The test object 60 can be a mobile phone or other manufactured object.

Figure 5:
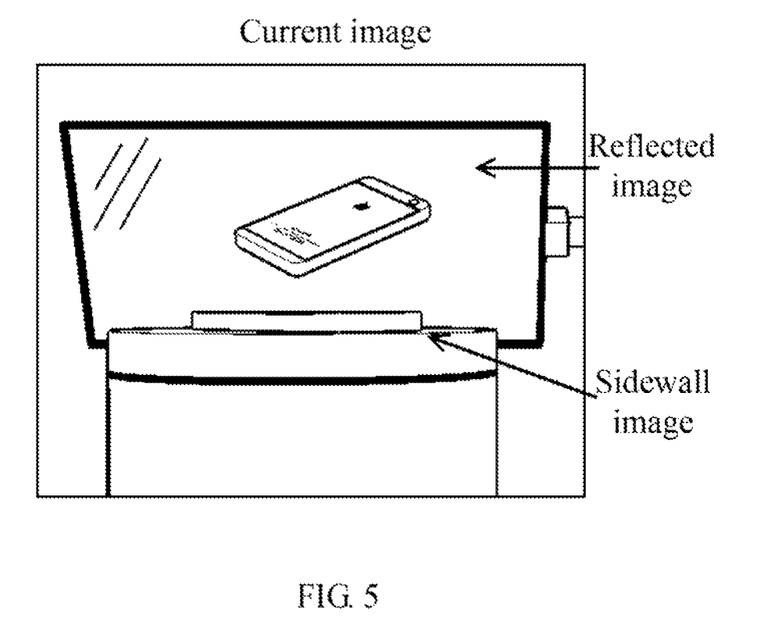
FIG. 5 is a diagrammatic view of one embodiment of a current image of the object including a sidewall image of the object and a reflected image of the object.

In one embodiment, the horizontal rotation platform 42 is connected to the plane mirror 45 through a connecting rod (not shown). The horizontal rotation platform 42 includes a driving motor (not shown) configured to rotate the horizontal rotation platform 42 to adjust the test object 60 to different angles. The driving motor can be a stepper motor or a servo motor. As shown in FIG. 5, the camera unit 40 simultaneously captures a sidewall image of sidewalls of the actual test object 60 placed on the horizontal rotation platform 42, and captures a reflected image of the test object 60 shown in the plane mirror 45.

Figure 2:
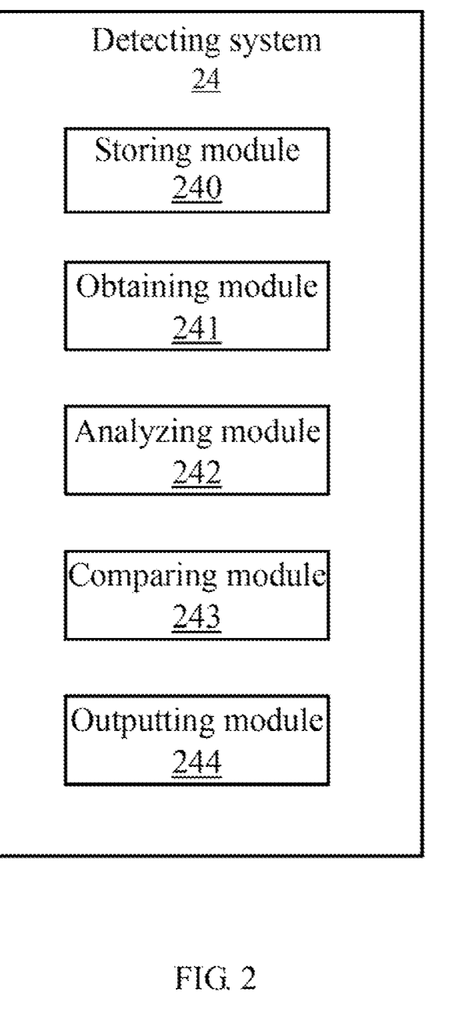
FIG. 2 is a block diagram of one embodiment of function modules of the detecting system in the electronic device of FIG. 1.

FIG. 2 is a block diagram of one embodiment of function modules of the detecting system 24. In at least one embodiment, the detecting system 24 can include a storing module 240, an obtaining module 241, an analyzing module 242, a comparing module 243, and an outputting module 244. The function modules 240-244 can include computerized code in the form of one or more programs, which are stored in the storage device 23. The at least one processor executes the computerized code to provide functions of the function modules 240-244.

Figure 6:
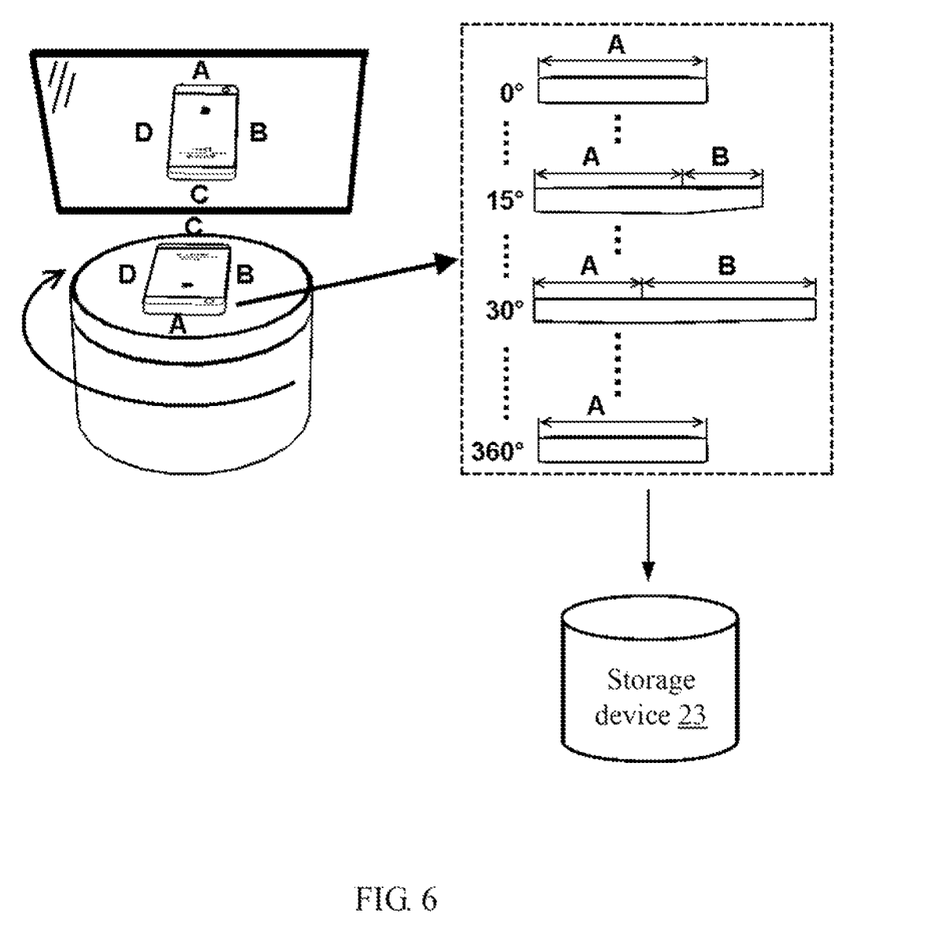
FIG. 6 is a diagrammatic view of one embodiment of standard sidewall images of a standard object in different rotation angles.

The storing module 240 is configured to store standard sidewall images of sidewalls of an ideal standard object, corresponding to different rotation angles of the standard object, to the storage device 23. The rotation angles of the standard object define angles to which the standard object are rotated by the horizontal rotation platform 42. Each standard sidewall image of the standard object records one or more sidewalls of the standard object and a position of each sidewall in a corresponding standard sidewall image. For example, the standard object (shown in FIG. 6) includes four sidewalls such as a sidewall A, a sidewall B, a sidewall C, and a sidewall D. A standard sidewall image corresponding to a rotation angle denoted as zero degrees includes the sidewall A of the standard object. A standard sidewall image corresponding to a rotation angle denoted as 30 degrees includes the sidewall A and the sidewall B of the standard object.

In one embodiment, before the standard sidewall images of the standard object are stored to the storage device 23, the storing module 240 controls the horizontal rotation platform 42 to rotate to different rotation angles, and controls the camera unit 40 to capture a standard current image of the standard object placed on the horizontal rotation platform 42 in each rotation angle of the standard object. Each standard current image of the standard object includes a standard sidewall image of sidewalls of the standard object placed on the horizontal rotation platform 42 and a standard reflected image of the standard object shown in the plane mirror 45. As shown in FIG. 5, a standard current image of the standard object includes a standard sidewall image and a standard reflected image.

Figure 7:
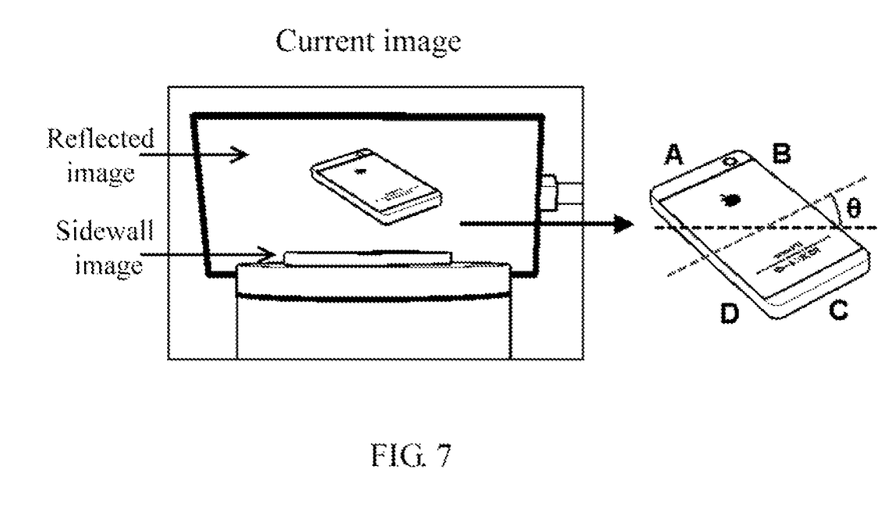
FIG. 7 is a diagrammatic view of one embodiment for calculating a rotation angle of the object.

In one embodiment, the storing module 240 is configured to recognize a position of a graphic item of each standard reflected image. The graphic item can be an icon or a character. The storing module 240 is configured to compare the position of the graphic item of each standard reflected image with a position of the graphic item of a standard reflected image of the standard object located at an initial position, and calculate each rotation angle of the standard object based on the result of comparison, as shown in FIG. 7. In one embodiment, the initial position is denoted as a zero starting position of the horizontal rotation platform 42. As shown in FIG. 5, when the horizontal rotation platform 42 is located at the initial position, the standard object is positioned horizontally and is fixed on the fixing unit.

In one embodiment, the storing module 240 is further configured to determine one or more sidewalls in a standard sidewall image according to a position of a graphic item of a corresponding standard reflected image in the same standard current image, calculate a reflected length of each sidewall using a sine formula based on the corresponding rotation angle, and determine the position of each sidewall in a standard sidewall image based on the reflected length of each sidewall of the standard sidewall image.

Figure 8:
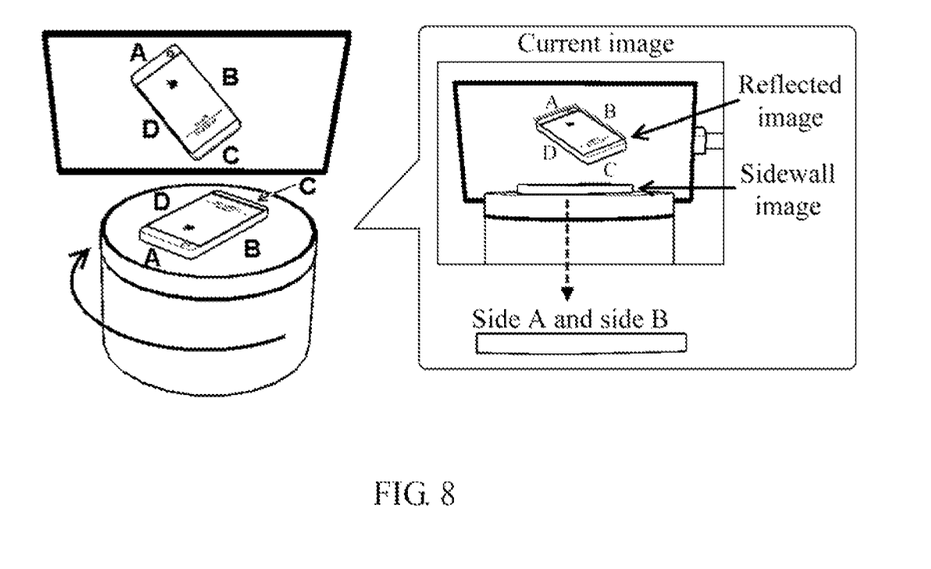
FIG. 8 is a diagrammatic view of one embodiment for determining one or more sidewalls in the sidewall image of the object.
Figure 9:
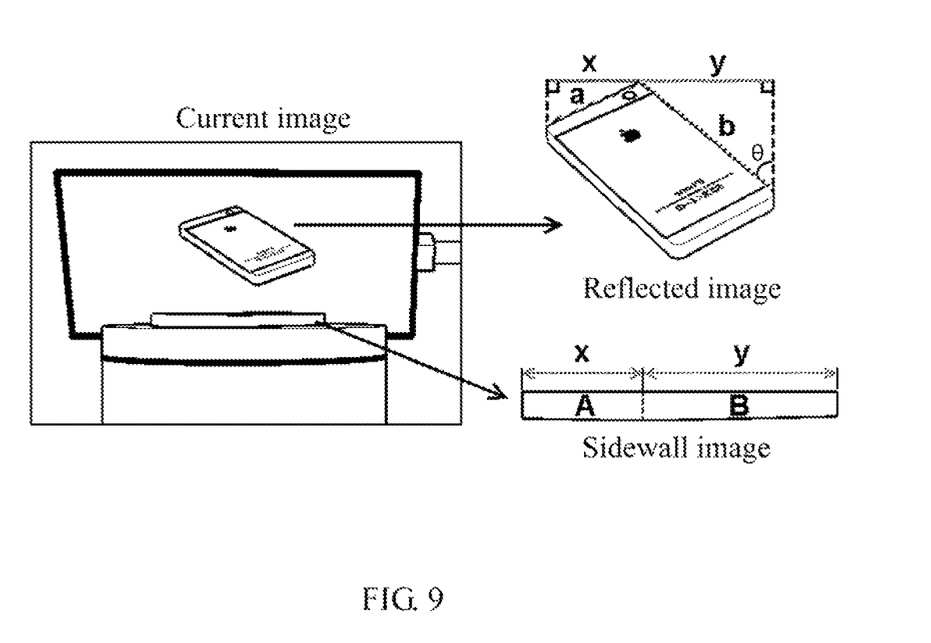
FIG. 9 is a diagrammatic view of one embodiment for determining a position of each sidewall in the sidewall image of the object.

As shown in FIG. 8, the storing module 240 is configured to determine that a standard sidewall image includes the sidewall A and the sidewall B. A rotation angle of the standard object is denoted as $\theta$, the length of the sidewall A is denoted as a length a, and the length of the sidewall B is denoted as a length b. A reflected length of the sidewall A is denoted as a length $x=\text{length } a\times\sin(\theta)$ according to the sine formula. A reflected length of the sidewall B is denoted as a length $y=\text{length } b\times\sin(\theta)$ according to the sine formula. The storing module 240 is configured to determine positions of the sidewall A and the sidewall B according to a proportionality between the length x and the length y.

When a test object 60 is placed on the horizontal rotation platform 42, and the horizontal rotation platform 42 is controlled to rotate, the obtaining module 241 request the detection device 4 to control the camera unit 40 to capture a current image of the test object 60. The current image of the test object 60 includes a sidewall image of sidewalls of the test object 60 and a reflected image of the test object 60 shown in the plane mirror 45. In one embodiment, the horizontal rotation platform 42 can rotate from an initial position denoted as zero degrees to a final position denoted as 360 degrees or any position therebetween.

The obtaining module 241 obtains the current image of the test object 60 from the camera unit 40.

The analyzing module 242 is configured to detect whether the sidewall image of the test object 60 has a surface flaw. In one embodiment, the analyzing module 242 is configured to recognize the surface flaw in the sidewall image using an image recognition software, such as a feature template matching software. In at least one embodiment, the analyzing module 242 is configured to recognize the sidewall image and the reflected image from the current image of the test object 60 using the image recognition software.

Figure 10:
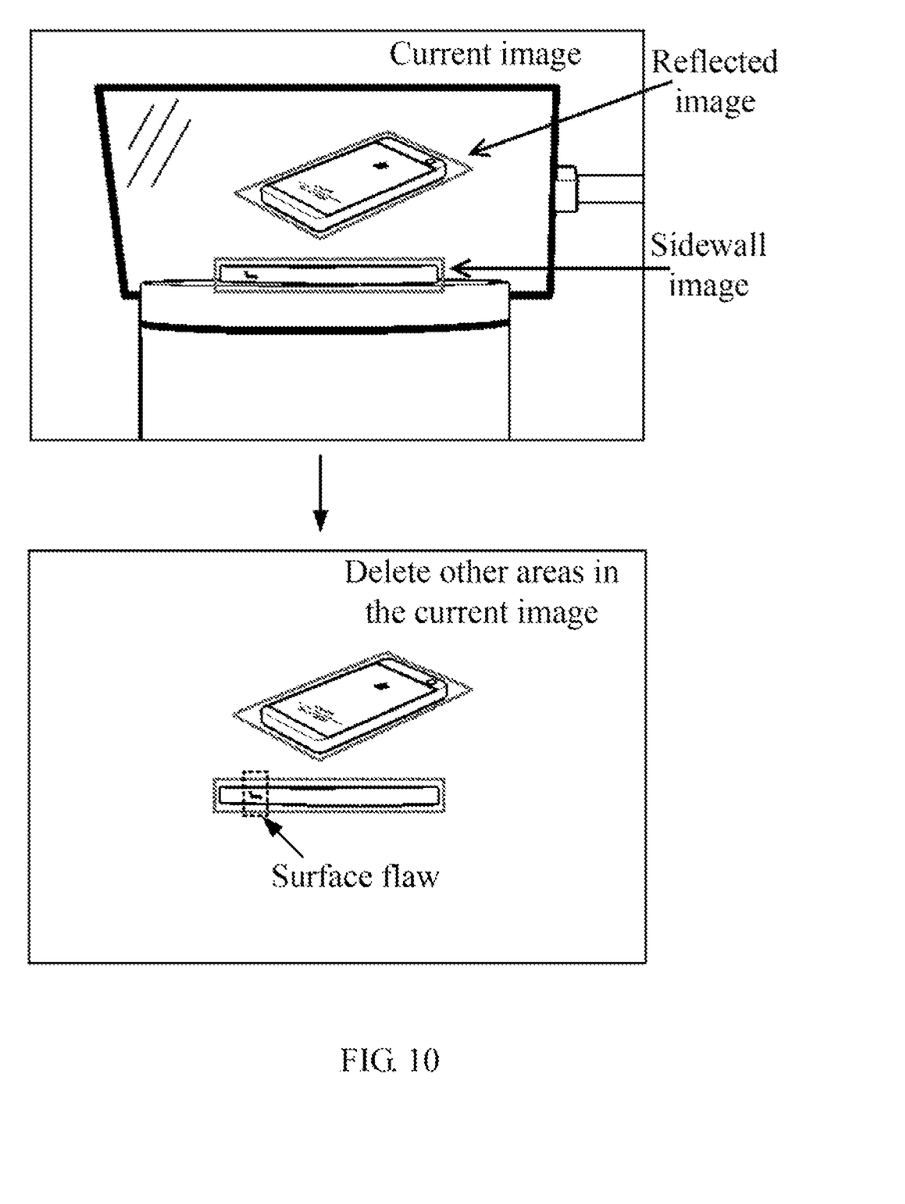
FIG. 10 is a diagrammatic view of one embodiment for detecting an area of the sidewall image and an area of the reflected image from the current image of the object in FIG. 5.

The analyzing module 242 is further configured to determine an area (e.g., a minimum bounding rectangle) of the sidewall image and an area of the reflected image, and delete other areas in the current image except for the determined areas, as shown in FIG. 10. The analyzing module 242 is further configured to detect whether the area of the sidewall image has the surface flaw.

The analyzing module 242 is configured to determine a rotation angle of the test object 60 based on the reflected image of the test object 60 when the sidewall image of the test object 60 has a surface flaw, and obtain a standard sidewall image of the standard object stored in the storage device 23 based on the rotation angle of the test object 60. For example, when the rotation angle of the test object 60 is 15 degrees, the analyzing module 242 can obtain a standard sidewall image of the standard object when the rotation angle of the standard object is 15 degrees. In at least one embodiment, the analyzing module 242 is configured to determine the rotation angle of the test object 60 according to a position of a graphic item of the reflected image.

Figure 11:
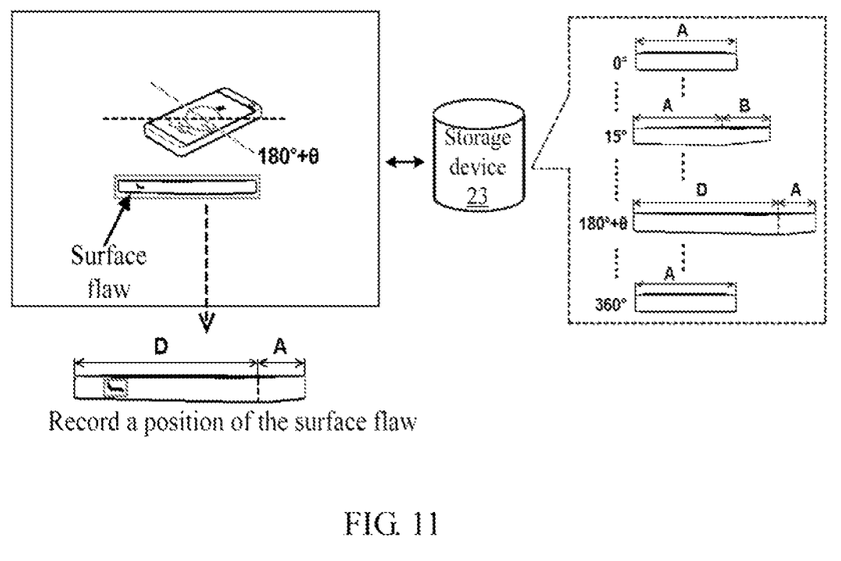
FIG. 11 is a diagrammatic view of one embodiment for comparing the sidewall image with the standard sidewall images in different rotation angles in FIG. 6.

The comparing module 243 is configured to compare the sidewall image of the test object 60 with the standard sidewall image of the standard object, and determine a position of the surface flaw on a sidewall of the test object based on the comparison. As shown in FIG. 11, the comparing module 243 is configured to compare the sidewall image of the test object 60 with a standard sidewall image of the standard object corresponding to a rotation angle (denoted as 180°+θ), and determines that the surface flaw is on a sidewall D of the test object 60.

In one embodiment, the outputting module 244 is configured to record the position of the sidewall of the test object that has the surface flaw, and display the position of the sidewall of the test object 60 on the display device 20. The outputting module 244 is further configured to sort the test object 60 according to a detection result, and display the detection result on the display device 20. The detection result can show that the test object 60 has no surface flaw, or can show that the test object 60 has one or more surface flaws.

In one embodiment, the outputting module 244 is configured to sort the test object 60 that has no surface flaw to a qualified object classification, and generate a prompt that the test object 60 passes inspection on the display device 20. The detection defines that the test object 60 does not have any surface flaw. The outputting module 244 sorts the test object 60 that has one or more surface flaws to an unqualified object classification, and generates a prompt that the test object 60 fails inspection on the display device 20.

In other embodiments, the detection system 24 can be in the detection device 4, or some modules of the detection system 24 are run in the detection device 4 and other modules of the detection system 24 are run in the electronic device 2. For example, the modules of 240-241 are executed by a microprocessor of the detection device 4, and the modules of 242-244 are executed by the processor 25 of the electronic device 2.

Figure 3:
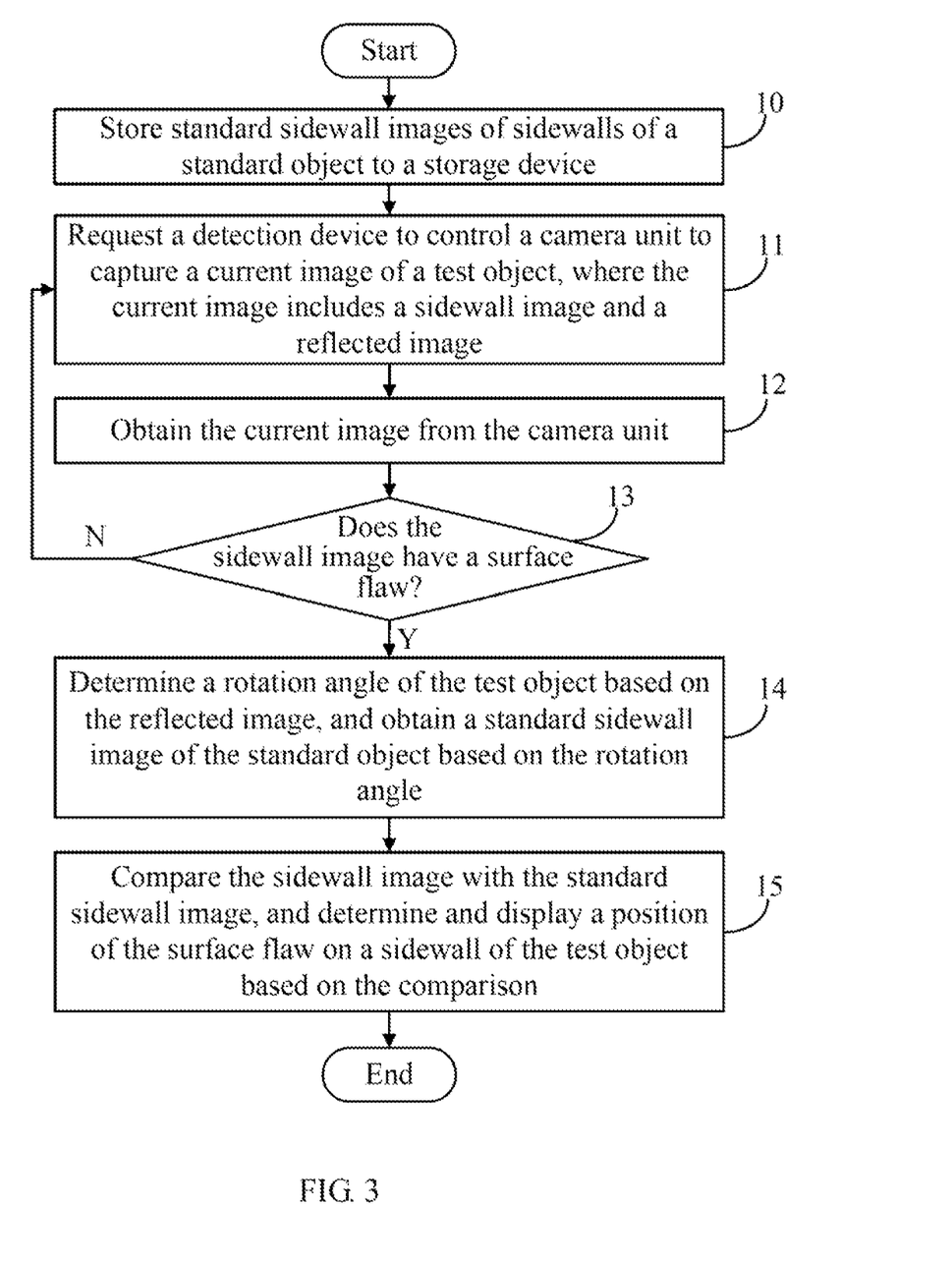
FIG. 3 illustrates a flowchart of one embodiment of a method for detecting a surface flaw of an object.

Referring to FIG. 3, a flowchart is presented in accordance with an example embodiment. The example method is provided by way of example, as there are a variety of ways to carry out the method. The method described below can be carried out using the configurations illustrated in FIGS. 1, and 2, for example, and various elements of these figures are referenced in explaining example method. Each block shown in FIG. 3 represents one or more processes, methods, or subroutines, carried out in the exemplary method. Additionally, the illustrated order of blocks is by example only and the order of the blocks can be changed. The exemplary method can begin at block 10. Depending on the embodiment, additional blocks can be added, others removed, and the ordering of the blocks can be changed.

In block 10, a storing module stores standard sidewall images of sidewalls of an ideal standard object corresponding to different rotation angles of the standard object, to a storage device. The rotation angles of the standard object define angles to which the standard object are rotated by the horizontal rotation platform 42. Each standard sidewall image of the standard object records one or more sidewalls of the standard object and a position of each sidewall in a corresponding standard sidewall image.

In block 11, an obtaining module request a detection device to control a camera unit to capture a current image of a test object. The current image of the test object includes a sidewall image of sidewalls of the test object and a reflected image of the test object shown in a plane mirror.

In block 12, the obtaining module obtains the current image of the test object from the camera unit.

In block 13, an analyzing module detects whether the sidewall image of the test object has a surface flaw. When the sidewall image of the test object has a surface flaw, block 14 is executed. When the sidewall image of the test object has no surface flaw, the procedure returns to execute block 11.

In block 14, the analyzing module determines a rotation angle of the test object based on the reflected image of the test object, and obtains a standard sidewall image of the standard object stored in the storage device, based on the rotation angle of the test object.

In block 15, a comparing module compares the sidewall image of the test object with the standard sidewall image of the standard object, and determines a position of the surface flaw on a sidewall of the test object based on the comparison.

In block 15, an outputting module further records the position of the sidewall of the test object that has the surface flaw, and displays the position of the sidewall of the test object on a display device. The outputting module further sorts the test object according to a detection result, and displays the detection result on the display device. As described above, the detection result can show that the test object has no surface flaw, or can show that the test object has one or more surface flaws.

In one embodiment, the outputting module sorts the test object that has no surface flaw to a qualified object classification, and generates a prompt that the test object passes inspection on the display device. The outputting module sorts the test object that has one or more surface flaws to an unqualified object classification, and generates a prompt that the test object fails inspection on the display device.

It should be emphasized that the above-described embodiments of the present disclosure, including any particular embodiments, are merely possible examples of implementations, set forth for a clear understanding of the principles of the disclosure. Many variations and modifications can be made to the above-described embodiment(s) of the disclosure without departing substantially from the spirit and principles of the disclosure. All such modifications and variations are intended to be included herein within the scope of this disclosure and protected by the following claims.

What is claimed is:

1. A computer-implemented method for detecting a surface flaw of an object using an electronic device in communication with a detection device, the method comprising:
   requesting the detection device to control a camera unit to capture a current image of a test object placed on a horizontal rotation platform of the detection device, wherein the current image of the test object comprises a sidewall image of sidewalls of the test object and a reflected image of the test object shown in a plane mirror of the detection device;
   obtaining the current image of the test object from the camera unit;
   detecting, at a processor of the electronic device, whether the sidewall image of the test object has a surface flaw;
   determining, at the processor upon detection of a surface flaw, a rotation angle of the test object based on the reflected image of the test object;

obtaining a standard sidewall image of a standard object stored in a storage device of the electronic device based on the rotation angle of the test object;

comparing the sidewall image of the test object with the standard sidewall image of the standard object;

determining a position of the surface flaw on a sidewall of the test object based on the comparison; and displaying the position of the surface flaw on the sidewall of the test object on a display device of the electronic device.

2. The method according to claim 1, further comprising:

storing standard sidewall images of sidewalls of a standard object corresponding to different rotation angles of the standard object to the storage device, wherein each standard sidewall image records one or more sidewalls of the standard object and a position of each sidewall in a corresponding standard sidewall image.

3. The method according to claim 2, wherein each rotation angle of the standard object is obtained by:

controlling the horizontal rotation platform to rotate to different rotation angles;

controlling the camera unit to capture a standard current image of the standard object placed on the horizontal rotation platform in each rotation angle of the standard object, wherein each standard current image of the standard object comprises a standard sidewall image of sidewalls of the standard object placed on the horizontal rotation platform and a standard reflected image of the standard object shown in the plane mirror;

recognizing a position of a graphic item of each standard reflected image of the standard object, wherein the graphic item is an icon or a character;

comparing the position of the graphic item of each standard reflected image with a position of the graphic item of a standard reflected image of the standard object located at an initial position; and calculating each rotation angle of the standard object based on the result of comparison.

4. The method according to claim 2, wherein the position of each sidewall in a standard side image is determined by:

calculating a reflected length of each sidewall using a sine formula based on the corresponding rotation angle; and determining the position of each sidewall in the standard side image based on the reflected length of each sidewall.

5. The method according to claim 1, further comprising:

recording the position of the sidewall of the test object that has the surface flaw;

sorting the test object that has no surface flaw to a qualified object classification, and generating a prompt that the test object passes inspection on the display device; and sorting the test object that has one or more surface flaws to an unqualified object classification, and generating a prompt that the test object fails inspection on the display device.

6. The method according to claim 1, wherein the test object is fixed on the horizontal rotation platform, and the camera unit and the plane mirror are arranged on two sides of the horizontal rotation platform.

7. An electronic device for detecting a surface flaw of an object, the electronic device in communication with a detection device, the electronic device comprising:

a camera unit;
a horizontal rotation platform;
a plane mirror;
a display device;
a processor; and
a storage device that stores one or more programs, when executed by the at least one processor, cause the at least one processor to:

request the detection device to control the camera unit to capture a current image of a test object placed on the horizontal rotation platform, wherein the current image of the test object comprises a sidewall image of sidewalls of the test object and a reflected image of the test object shown in the plane mirror;

obtain the current image of the test object from the camera unit;

detect, at the processor, whether the sidewall image of the test object has a surface flaw;

determine, at the processor upon detection of a surface flaw, a rotation angle of the test object based on the reflected image of the test object;

obtain a standard sidewall image of a standard object stored in the storage device based on the rotation angle of the test object;

compare the sidewall image of the test object with the standard sidewall image of the standard object;

determine a position of the surface flaw on a sidewall of the test object based on the comparison; and display the position of the surface flaw on the sidewall of the test object on the display device.

8. The electronic device according to claim 7, wherein the one or more programs further cause the at least one processor to:

store standard sidewall images of sidewalls of a standard object corresponding to different rotation angles of the standard object to the storage device, wherein each standard sidewall image records one or more sidewalls of the standard object and a position of each sidewall in a corresponding standard sidewall image.

9. The electronic device according to claim 8, wherein each rotation angle of the standard object is obtained by:

controlling the horizontal rotation platform to rotate to different rotation angles;

controlling the camera unit to capture a standard current image of the standard object placed on the horizontal rotation platform in each rotation angle of the standard object, wherein each standard current image of the standard object comprises a standard sidewall image of sidewalls of the standard object placed on the horizontal rotation platform and a standard reflected image of the standard object shown in the plane mirror;

recognizing a position of a graphic item of each standard reflected image of the standard object, wherein the graphic item is an icon or a character;

comparing the position of the graphic item of each standard reflected image with a position of the graphic item of a standard reflected image of the standard object located at an initial position; and calculating each rotation angle of the standard object based on the result of comparison.

10. The electronic device according to claim 8, wherein the position of each sidewall in a standard side image is determined by:

calculating a reflected length of each sidewall using a sine formula based on the corresponding rotation angle; and determining the position of each sidewall in the standard side image based on the reflected length of each sidewall.

11. The electronic device according to claim 7, wherein the one or more programs further cause the at least one processor to:

record the position of the sidewall of the test object that has the surface flaw;

sort the test object that has no surface flaw to a qualified object classification, and generate a prompt that the test object passes inspection on the display device; and sort the test object that has one or more surface flaws to an unqualified object classification, and generate a prompt that the test object fails inspection on the display device.

12. The electronic device according to claim 7, wherein the test object is fixed on the horizontal rotation platform, and the camera unit and the plane mirror are arranged on two sides of the horizontal rotation platform.

13. A non-transitory storage medium having stored thereon instructions that, when executed by a processor of an electronic device, causes the processor to perform a method for detecting a surface flaw of an object, the electronic device in communication with a detection device, wherein the method comprises:

requesting the detection device to control a camera unit to capture a current image of a test object placed on a horizontal rotation platform of the detection device, wherein the current image of the test object comprises a sidewall image of sidewalls of the test object and a reflected image of the test object shown in a plane mirror of the detection device;

obtaining the current image of the test object from the camera unit;

detecting, at a processor of the electronic device, whether the sidewall image of the test object has a surface flaw;

determining, at the processor upon detection of a surface flaw, a rotation angle of the test object based on the reflected image of the test object;

obtaining a standard sidewall image of a standard object stored in a storage device of the electronic device based on the rotation angle of the test object;

comparing the sidewall image of the test object with the standard sidewall image of the standard object; and determining a position of the surface flaw on a sidewall of the test object based on the comparison; and displaying the position of the surface flaw on the sidewall of the test object on a display device of the electronic device.

14. The non-transitory storage medium according to claim 13, wherein the method further comprises:

storing standard sidewall images of sidewalls of a standard object corresponding to different rotation angles of the standard object to the storage device, wherein each standard sidewall image records one or more sidewalls of the standard object and a position of each sidewall in a corresponding standard sidewall image.

15. The non-transitory storage medium according to claim 14, wherein each rotation angle of the standard object is obtained by:

controlling the horizontal rotation platform to rotate to different rotation angles;

controlling the camera unit to capture a standard current image of the standard object placed on the horizontal rotation platform in each rotation angle of the standard object, wherein each standard current image of the standard object comprises a standard sidewall image of sidewalls of the standard object placed on the horizontal rotation platform and a standard reflected image of the standard object shown in the plane mirror;

recognizing a position of a graphic item of each standard reflected image of the standard object, wherein the graphic item is an icon or a character;

comparing the position of the graphic item of each standard reflected image with a position of the graphic item of a standard reflected image of the standard object located at an initial position; and calculating each rotation angle of the standard object based on the result of comparison.

16. The non-transitory storage medium according to claim 14, wherein the position of each sidewall in a standard side image is determined by:

calculating a reflected length of each sidewall using a sine formula based on the corresponding rotation angle; and determining the position of each sidewall in the standard side image based on the reflected length of each sidewall.

17. The non-transitory storage medium according to claim 13, wherein the method further comprises:

recording the position of the sidewall of the test object that has the surface flaw;

sorting the test object that has no surface flaw to a qualified object classification, and generating a prompt that the test object passes inspection on the display device; and sorting the test object that has one or more surface flaws to an unqualified object classification, and generating a prompt that the test object fails inspection on the display device.

18. The non-transitory storage medium according to claim 13, wherein the test object is fixed on the horizontal rotation platform, and the camera unit and the plane mirror are arranged on two sides of the horizontal rotation platform.

* * * * *